United States Patent
Jung et al.

[11] Patent Number: 6,165,672
[45] Date of Patent: Dec. 26, 2000

[54] MALEIMIDE OR ALICYCLIC OLEFIN-BASED MONOMERS, COPOLYMER RESIN OF THESE MONOMERS AND PHOTORESIST USING THE RESIN

[75] Inventors: Jae Chang Jung; Keun Kyu Kong; Cheol Kyu Bok; Ki Ho Baik, all of Ichon, Rep. of Korea

[73] Assignee: Hyundai Electronics Industries Co., Ltd., Rep. of Korea

[21] Appl. No.: 09/152,976

[22] Filed: Sep. 14, 1998

[30] Foreign Application Priority Data

Nov. 1, 1997 [KR] Rep. of Korea ...................... 97-57573

[51] Int. Cl.$^7$ .............................. G03C 1/73; G03F 7/004; C08L 35/00; C08L 45/00; H01L 29/12
[52] U.S. Cl. ......................... 430/270; 430/905; 430/914; 430/9; 44/346; 525/282; 525/205; 524/532; 524/553; 526/281; 526/280
[58] Field of Search ............................... 44/346; 525/282, 525/205; 524/532, 553; 526/281, 280; 430/270.1, 326, 910, 908, 914, 905, 9, 18

[56] References Cited

U.S. PATENT DOCUMENTS

| | | |
|---|---|---|
| 4,011,386 | 3/1977 | Matsumoto et al. . |
| 4,106,943 | 8/1978 | Ikeda et al. . |
| 4,491,628 | 1/1985 | Ito et al. .................................. 430/176 |
| 4,883,740 | 11/1989 | Schwalm et al. ........................ 430/270 |
| 5,087,677 | 2/1992 | Brekner et al. ........................... 526/160 |
| 5,212,043 | 5/1993 | Yamamoto et al. ..................... 430/192 |
| 5,252,427 | 10/1993 | Bauer et al. ............................. 430/270 |
| 5,278,214 | 1/1994 | Moriya et al. . |
| 5,849,808 | 12/1998 | Schacht et al. ........................... 322/31 |

FOREIGN PATENT DOCUMENTS

| | | |
|---|---|---|
| 794458 | 9/1997 | European Pat. Off. . |
| 0836119A1 | 11/1997 | European Pat. Off. . |
| 05297591 | 11/1993 | Japan . |
| 05310885 | 11/1993 | Japan . |
| 10213912 | 8/1998 | Japan . |
| 10218941 | 8/1998 | Japan . |
| 128164 | 2/1977 | Netherlands . |
| 1329997 | 9/1970 | United Kingdom . |
| WO 96/37526 | 11/1996 | WIPO . |
| WO 97/33198 | 9/1997 | WIPO . |
| WO98/07759 | 2/1998 | WIPO . |

OTHER PUBLICATIONS

Thomas I. Wallow, et al., "Evaluation of Cycloolefin–Maleic Anhydride Alternating Copolymers as Single–Layer Photoresist for 193nm Phololithography", 1996, Proc. SPIE, vol. 2724, 355–364.

R.D. Allen et al., "The Influence of Photoacid Structure on the Design and Performance of 193nm Resists", 1997, Journal of Photopolymer Science and Technology, vol. 10, 503–510.

F.M. Houlihan et al., "A Commercially Viable 193nm single Layer Resist Platform", 1997, Journal of Photopolymer Science and Technology, vol. 10, 511–520.

J.C. Jung et al., "Arf Single Layer Resist Composed of Alicyclic Main Chain Containing Maleic Anhydride ", 1997, Journal of Photopolymer Science and Technology, vol. 10, 529–533.

(List continued on next page.)

Primary Examiner—Janet Baxter
Assistant Examiner—Sin J. Lee
Attorney, Agent, or Firm—Townsend and Townsend and Crew LLP

[57] ABSTRACT

The present invention relates to a novel maleimide- or alicyclic olefin-based monomer, a copolymer resin of these monomers and a photoresist using the copolymer resin. The maleimide-introduced copolymer resin according to the present invention can easily be copolymerized with alicyclic olefin unit, has a physical property capable of enduring in 2.38% TMAH developer and increases adhesion of ArF or KrF photoresist. The photoresist film using a copolymer resin according to the present invention can be applied to highly integrate semiconductor devices.

31 Claims, 6 Drawing Sheets

OTHER PUBLICATIONS

S.J. Choi et al., "New ArF Single–Layer Resist for 193–nm Lithography", 1997, Journal of Photopolymer Science and Technology, vol. 10, 521–528.

K. Nakano et al., "Chemically Amplified Resist Based on High Etch–Resistant Polymer for 193–nm Lithography", 1997, Journal of Photopolymer Science and Technology, vol. 10, 561–569.

CA Register No. 100207–98–5.

CA Register No. 32759–57–2.

CA Register No. 27056–70–8.

CA Register No. 174659–58–6.

CA Register No. 28503–41–5.

CA Register No. 194997–59–6.

CA Abstract No. 104:149512 & Macromolecules 19(4) 1266–8 (1986).

CA Abstract No. 91:124064 & Makromol. Chem. 180(8) 1975–88 (1979).

CA Abstract No. 113:24734 & JP 02 051511.

CA Abstract No. 127:227269 & J Photopolym. Sci. Technol. 10(4) 529–534 (1997).

CA Abstract No. 124:317926 & Marcomol. Rapid Commun. 17(3) 173–180 (1996).

CA Abstract No. 124:203171 & Macromolecules 29(8) 2755–63 (1996).

CA Abstract No. 127:227308 & Proc. SPIE–Int. Soc. Opt. Eng. (1997) 3049 Advances in Resist Technology and Processing XIV 92–103.

CA Abstract No. 66:18889 & Magy. Kem. Foly. (1996) 72(11)491–3.

CA Abstract No. 199328–07–9.

"Synthesis and Dissolution Characteristics of Novel Alicyclic Polymers with Monoacid Ester Structures", Takashi Hattori, et al., pp. 535–544, *Journal of Photopolymer Science and Technology*, vol. 10, No. 4 (1997).

"New Protective Groups in Alicyclic Methacrylate Polymers for 193–nm Resists", Koji Nozaki and Ei Yano, pp. 545–550, *Journal of Photopolymer Science and Technology*, vol. 10, No. 4 (1997).

Enomoto et al 129:223219, File HCA of STN Database Service, Chemical abstracts, American chemical society, Englis Abstract of JP 10213912, 1998.

Fukura et al 121:10910, File HCA of STN Database SVC., Chemical abstracts, American Chemical Society, English Abstract of JP 05310885, 1994.

Ito 129:209337, File HCA of STN Database SVC., Chemical abstracts, American Chemical Society, English Abstract of JP 10218941, 1998.

Nozaki et al, 120:285044, File HCA of STN Database SVC., Chemical abstracts, American Chemical Society, English Abstract of JP 05297591, 1994.

MALEIMIDE OR ALICYCLIC OLEFIN-BASED MONOMERS, COPOLYMER RESIN OF THESE MONOMERS AND PHOTORESIST USING THE RESIN

BACKGROUND OF THE INVENTION

The present invention relates to novel maleimide and alicylic olefin-based monomers, a copolymer resin of these monomers, and a photoresist using the copolymer resin. More specifically, the present invention relates to a maleimide- or alicyclic olefin-based monomer useful for a photoresist usable for lithography process using ultra-short wavelength light source such as KrF($\lambda$=248 $\mu$m), ArF($\lambda$=193 $\mu$m), X-ray, ion beam, E-beam and EUV(Extreme Ultra Violet) which is a potentially applicable technology to the fabrication of a fine circuit of a highly integrated semiconductor device. The present invention also relates to a copolymer resin of these monomers and to a photoresist formulated by using the copolymer resin.

Recently, attempts to highly integrate a semiconductor device have had a big influence on the development of fabrication techniques for photoresist patterns. To prepare a semiconductor device, it is necessary to formulate a photoresist pattern, which is widely used in masking such as etching or ion injection.

The general mechanism of formulating a photoresist pattern is as follows. First, polymer and photoacid generator are dissolved in solvent in a certain ratio to give a photoresist solution. This photoresist solution is coated on a wafer substrate of semiconductor device, and then selectively exposed through a mask to a light source. The exposed wafer is soft-baked to remove an exposed or un-exposed region of the photoresist by using a weak alkaline developing solution, such as tetramethyl ammonium hydroxide (TMAH). The soft-baked wafer is washed with deionized water and dried to formulate a photoresist pattern.

The relation between photoresist resolution and wavelength of light source in photolithography is shown by the following formula:

$$R = k \ast \lambda / NA$$

wherein R is a resolution, k is a process constant, $\lambda$ is wavelength of a light source, and NA is a numerical aperture. As shown in the above formula, the resolution (R) of a photoresist pattern is proportional to the wavelength ($\lambda$) and the process constant (k), and is in inversely proportional to the numerical aperture (NA) of laser stepper. Thus, to increase the light resolution, the wavelength of light source must be shortened. For instance, G-line and I-line laser steppers which are 436 nm and 365 nm in wavelength are limited to about 0.7 $\mu$m and 0.5 $\mu$m in the process resolution, respectively.

In attempts to formulate a fine pattern of 0.5 $\mu$m or less, a stepper using a deep ultra violet (DUV) light source of a short wavelength, such as KrF laser ($\lambda$=248 nm) or ArF laser ($\lambda$=193 nm), a contrast enhancement layer (CEL) process by which a separate thin film capable of improving image contrast is formulated on the wafer, a process for using a phase reversal mask, or a silylation process for silylating a surface of photoresist film have been proposed. However, these processes are complicated and yield is lowered. Therefore, a laser stepper using DUV light source has been developed as the most simple process. In this regard, a photoresist for DUV light source has also been developed.

As a photoresist for DUV light source, chemical amplification photoresists have been the prevailing choice in semiconductor devices, because they are highly sensitive to DUV light, which is now recognized as light source suitable for accomplishing the high integration of semiconductor devices. The chemical amplification photoresist consists generally of a photoacid generator and a matrix polymer having a chemical structure which sensitively reacts with acid.

The mechanism of such a chemical amplification photoresist is as follows. The photoresist is exposed through a mask to a ultra violet light source. An acid is generated by the action of the photoacid generator which then, reacts with the main or side chain of the matrix polymer. This reaction surprisingly increases the solubility of the copolymer in the developing solution by changing the structure of the polymer, e.g., by decomposing it, cross-linking it or changing its polarity. Therefore, at exposed regions the copolymer is dissolved in the developing solution, whereas at un-exposed regions the copolymer has no change in its original structure and remains undissolved in the developing solution, so that the shape of the mask may leave as a positive image on a substrate. In the above lithographic process, since the resolution depends on the wavelength of light source, the smaller the wavelength of light source, the finer the pattern formulated.

In general, a photoresist is required to have high etch resistance, thermal resistance and adhesion. In addition, the photoresist film used in semiconductor devices must be developed in 2.38% TMAH aqueous solution. However, it would be difficult to prepare a copolymer resin which satisfies all the properties of photoresist. For instance, the copolymer resin having polyacrylate-based main chain structure can be easily synthesized, but it is difficult to get etching resistance and to use 2.38% TMAH in development process.

The etching resistance can be improved by introducing alicyclic unit into main chain of the copolymer resin, but it is difficult to substitute the entire main chain by alicyclic unit. When a metal is used as a catalyst, the entire main chain may be substituted by alicyclic moiety. However, in this instance, removal of the metal component contained in the resin is difficult and the metal component may give a fatal unfavorable effect on the semiconductor device.

In the other hand, Bell Lab. has proposed a copolymer resin of the following formula (1), having a main chain structure substituted by norbornene, acrylate and maleic anhydride.

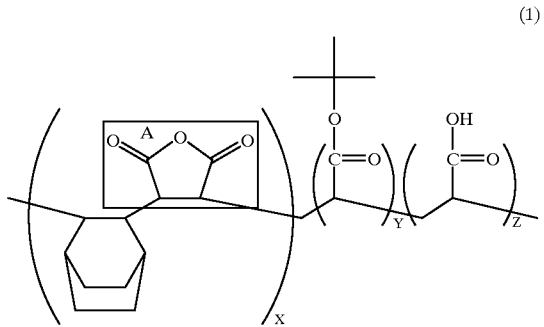

(1)

In this copolymer resin, maleic anhydride, A-moiety of the formula (1), used for the polymerization of an alicyclic olefin group does not absorb a light of 193 nm in wavelength and is the only material capable of polymerizing with the alicyclic unit, i.e., norbornene. However, the maleic anhydride, upon non-exposure, is easily dissolved in 2.38%

TMAH aqueous solution and occurs top-loss phenomenon in which the top of the photoresist pattern becomes round. Therefore, this copolymer resin is not suitable to the resin for KrF or ArF lithography process.

Accordingly, to inhibit dissolution, it is necessary to increase the ratio of t-butyl substituent, y-moiety of the formula (1). In this instance, the ratio of carboxylate substituent, z-moiety of the formula (1), which increases the adhesion is reduced and thus, the photoresist is departed from the wafer upon actual patterning and the pattern formulation is not possible.

In addition, upon post exposure delay which does not involve a baking immediately after exposure, the bottom of the pattern is shorter than the top of the pattern. That is, T-top phenomenon occurs, and thus the pattern formulation itself is not possible. Also, since maleic anhydride reacts with hydroxyl groups (—OH) which increase adhesion, there is a possibility of influencing shelf life of the photoresist.

Bell Lab. has attempted to solve such disadvantages by introducing as a bi-component dissolution inhibitor, an alternating copolymer of cycloolefin and maleic anhydride. However, since this method must use a dissolution inhibitor in the excess amount, about 30% by weight of the copolymer resin, reproductivity of the resin is low and the cost is increased. Accordingly, this resin also is not suitable as a photoresist resin.

SUMMARY OF THE INVENTION

As a first aspect, the present invention provides a maleimide-based monomer represented by the following formula (2):

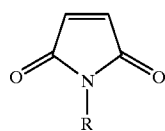

(2)

wherein R is selected from the group consisting of main or side chain-substituted alkyls having 1 to 10 carbon atoms, main or side chain-substituted primary, secondary or tertiary alcohols having 1 to 10 carbon atoms, and main or side chain-substituted diols having 1 to 10 carbon atoms.

As a second aspect, the present invention provides a process for preparing the maleimide-based monomer of formula (2).

The process comprises reacting a reactant selected from the group consisting of ethanolamine, aminopropanol, 1-amino-2-propanol, 2-amino-1-propanol, 2-amino-1-butanol, 4-amino-1-butanol, and 2-amino-2-methyl-1-propanol, with maleic anhydride, and imidizing the reaction product in the presence of acetic anhydride to produce the maleimide-based monomers of formula (2).

As a third aspect, the present invention provides another process for preparing the maleimide-based monomer of formula (2). The process comprises reacting $K_2CO_3$, NaOH or tetramethyl ammonium hydroxide aqueous solution with an acetate reactant selected from the group consisting of 2-maleimidethyl acetate, 3-maleimidepropyl acetate, 1-maleimideisopropyl acetate, 2-maleimidepropyl acetate, 2-maleimidebutyl acetate, 4-maleimidebutyl acetate, and 2-maleimide-2-methylpropyl acetate to produce the maleimide-based monomers of formula (2).

As a fourth aspect, the present invention provides an alicyclic olefin-based monomer represented by the following formulas (3) or (4):

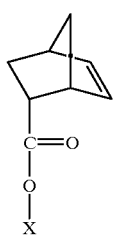

(3)

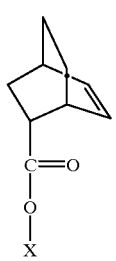

(4)

wherein X is selected from the group consisting of hydrogen, t-butyl and 2-hydroxyethyl.

As a fifth aspect, the present invention provides a process for preparing the alicyclic olefin-based monomer of the formulas (3). The process comprises reacting cyclopentadiene with an acrylate reactant selected from the group consisting of acrylic acid, 2-hydroxyethyl acrylate, and t-butyl acrylate, to produce the alicyclic olefin-based monomers of the formulas (3).

As a sixth aspect, the present invention provides another process for preparing the alicyclic olefin-based monomer of the formulas (4). The process comprises reacting cyclohexadiene with an acrylate reactant selected from the group consisting of acrylic acid and 2-hydroxyethyl acrylate t-butyl acrylate to produce the alicyclic olefin-based monomers of the formulas (4).

As another aspect, the present invention provides a copolymer resin for KrF or ArF photoresist consisting of at least one maleimide-based monomer of formula (2) and/or maleic anhydride, together with at least one alicyclic olefin-based monomer of the formulas (3) or (4).

As yet another aspect, the present invention provides a process for preparing the copolymer resin of the invention which comprises polymerizing at least one maleimide-based monomer of formula (2), with at least one alicyclic olefin-based monomer of formulas (3) or (4) in the presence of a polymerization initiator. The process also includes the optional co-polymerization with maleic anhydride as well. The invention also provides specific methods for preparing copolymer resins including poly[2-maleimidylethanol/t-butyl 5-norbornene-2-carboxylate/2-hydroxyethyl 5-norbornene-2-carboxylate/5-norbornene-2-carboxylic acid], poly[3-maleimidylpropanol/t-butyl-5-norbonen-2-carboxylate/2-hydroxyethyl 5-norbornene-2-carboxylate/5-norbornene- 2-carboxylic acid], poly[2-maleimidylehtanol/ maleic anhydride/t-butyl 5-norbornene-2-carboxylate/2-hydroxyethyl 5-norbornene-2-carboxylate/5-norbornene-2-carboxylic acid], poly[3-maleimidylpropanol/maleic anhydride/ t-butyl 5-norbornene-2-carboxylate/2- hydroxyethyl 5- norbornene-2-carboxylate/5-norbornene-2- carboxylic acid], poly[2-maleimidylethyl acetate/t-butyl 5-norbornene-2-carboxylate/2-hydroxyethyl 5-norbornene-2-carboxylate/5-norbornene-2-carboxylic acid], and poly[3-maleimidepropyl acetate/t-butyl 5- norbornene-2-carboxylate/2-hydroxyethyl 5-norbornene-2-carboxylate/5-norbornene-2-carboxylic acid].

As another aspect, the present invention provides a photoresist comprising the copolymer resin of the invention, a photoacid generator and a solvent, and a method for preparing the photoresist. The method comprises the steps: (i) dissolving in a solvent, a copolymer resin consisting of at least one maleimide-based monomer of formula (2) and/or maleic anhydride, and at least one alicyclic olefin-based monomer of the formulas (3) or (4), (ii) stirring the reaction product of step (i) with photo acid generator; and (iii) filtering the reaction product of step (ii).

As another aspect, the present invention provides a semiconductor device comprising the photoresist of the invention.

DESCRIPTION OF THE PREFERRED EMBODIMENT

Figure 1:
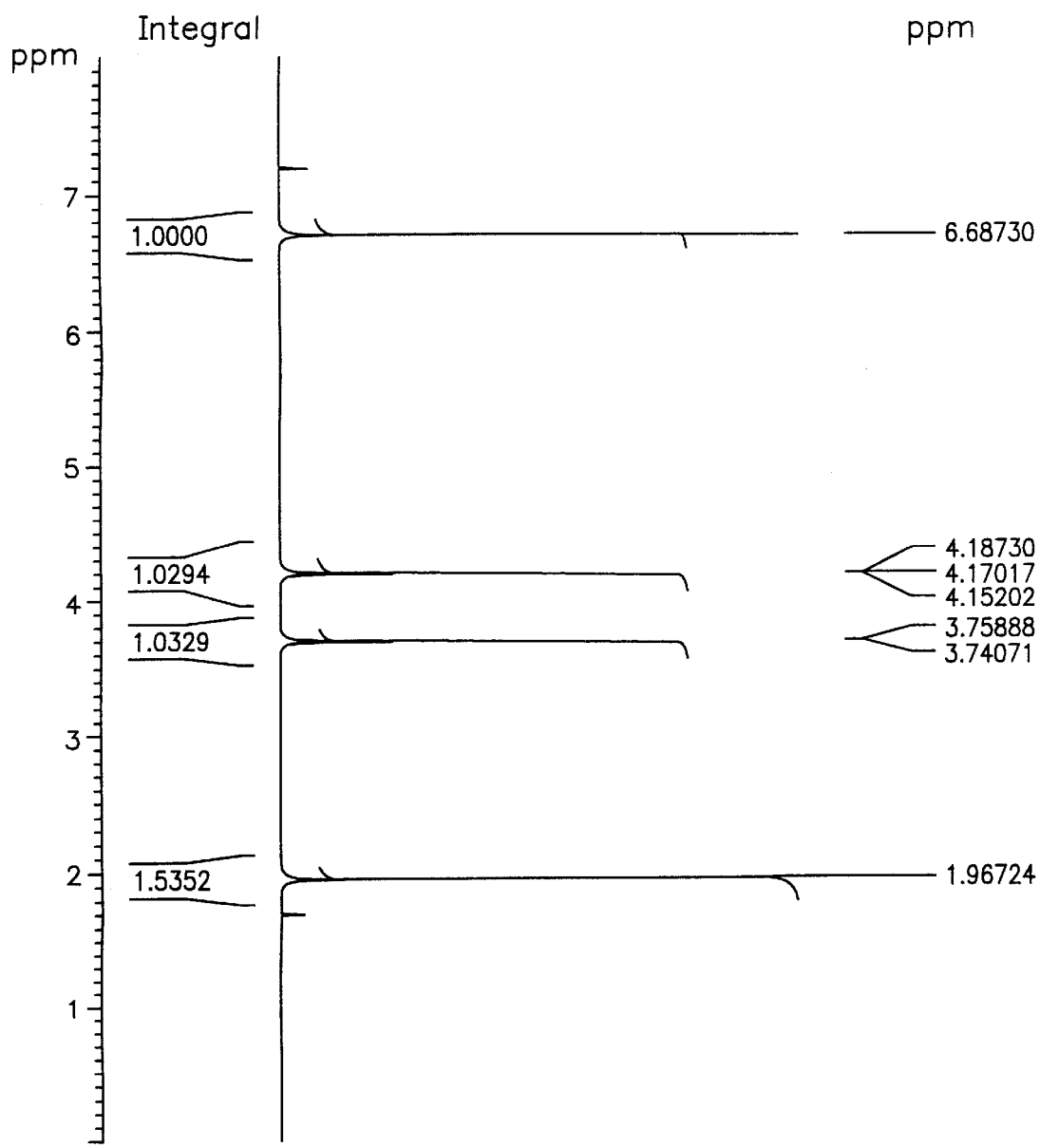
FIG. 1 is the NMR spectra of monomer (5) obtained through the process of Example 1.

The present inventors have extensively studied and experimented to develop a copolymer resin which satisfies all of the properties of a photoresist. As a result, we have found that a maleimide-introduced photoresist resin can easily be copolymerized with an alicyclic olefin unit, has a physical property capable of enduring in 2.38% TMAH developer, and shows increased adhesion of KrF or ArF photoresist.

Thus, it is a primary object of the present invention to provide a novel maleimide-based monomer represented by the following formula (2):

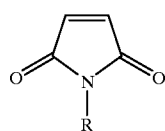

(2)

wherein R is selected from the group consisting of main or side chain-substituted alkyls having from 1 to 10 carbon atoms, main or side chain-substituted primary, secondary or tertiary alcohols having from 1 to 10 carbon atoms, and main or side chain-substituted diols having from 1 to 10 carbon atoms. It is a further object of the present invention to provide a process for the preparation these monomers.

Another object of the present invention is to provide a novel alicyclic olefin-based monomer represented by the following formulas (3) and (4):

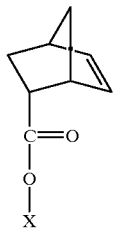

(3)

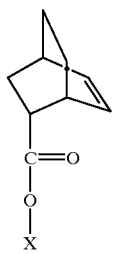

(4)

wherein X is selected from the group consisting of hydrogen, t-butyl or 2-hydroxyethyl. It is a further object of the present invention to provide a process for the preparation these monomers.

A further object of the present invention is to provide a novel copolymer resin consisting of at least one maleimide-based monomer of the formula (2) and/or maleic anhydride, together with at least one alicyclic olefin-based monomer of the formulas (3) or (4), and a process for the preparation thereof.

A still further object of the present invention is to provide a photoresist formulated by using the copolymer resin of the present invention, and a process for the preparation thereof.

Finally, another object of the present invention is to provide a process for preparing a semiconductor device by using the photoresist of the invention.

Among the maleimide-based monomers of formula (2) according to the present invention, 2-maleimidethyl acetate, 3-maleimidepropyl acetate, 1-maleimideisopropyl acetate, 2-maleimidepropyl acetate, 2-maleimidebutyl acetate, 4-maleimidebutyl acetate, 2-maleimide- 2-methylpropyl acetate, 2-maleimidylethanol, 3-maleimidyl propanol, 2-maleimidylpropanol, 1-maleimidylisopropanol, 2-maleimidyl-1- butanol, 4-maleimidyl-1-butanol, 2-maleimidyl-2-methyl-1-propanol or the mixtures thereof are preferred.

The maleimide-based monomer of formula (2) according to the present invention may be prepared using a number of different techniques set forth in steps (a) to (g) below. In general, the maleimide-based monomer of formula (2) can be prepared by a reactant selected from the group consisting of ethanolamine, aminopropanol, 1-amino-2-propanol, 2-amino-1-propanol, 2-amino-1-butanol, 4-amino-1-butanol, and 2-amino-2-methyl- 1-propanol, with maleic anhydride, and imidizing the reaction product in the presence of acetic anhydride. According to a second method, the maleimide-based monomers of formula (2) can be prepared by reacting $K_2CO_3$, NaOH or tetramethyl ammonium hydroxide aqueous solution with an acetate reactant selected from the group consisting of 2-maleimidethyl acetate, 3-maleimidepropyl acetate, 1-maleimideisopropyl acetate, 2-maleimidepropyl acetate, 2-maleimidebutyl acetate, 4-maleimidebutyl acetate, and 2-maleimide-2-methylpropyl acetate.

For example, the following methods can be employed to produce the maleimide-based monomers of formula (2): (a) reacting ethanolamine with maleic anhydride and imidizing the reaction product in the presence of acetic anhydride to produce 2-maleimidethyl acetate; or (b) reacting aminopropanol with maleic anhydride and imidizing the reaction product in the presence of acetic anhydride to produce 3-maleimidepropyl acetate; or (c) reacting 1-amino-2-propanol with maleic anhydride and imidizing the reaction product in the presence of acetic anhydride to produce 1-maleimideisopropyl acetate; or (d) reacting 2-amino-1-propanol with maleic anhydride and imidizing the reaction product in the presence of acetic anhydride to produce 2-maleimidepropyl acetate; or (e) reacting 2-amino-1-butanol with maleic anhydride and imidizing the reaction product in the presence of acetic anhydride to produce 2-maleimidebutyl acetate; or (f) reacting 4-amino-1-butanol with maleic anhydride and imidizing the reaction product in the presence of acetic anhydride to produce 4-maleimidebutyl acetate; or (g) reacting 2-amino-2-methyl-1-propanol with acetic anhydride and imidizing the reaction product in the presence of maleic anhydride to produce 2-maleimide-2-methylpropyl acetate.

Specifically, maleic anhydride was dissolved in purified tetrahydrofuran solvent. To the mixture was slowly added ethanolamine, aminopropanol, 1-amino-2-propanol, 2-amino-1-propanol, 2-amino-1-butanol, 4-amino-1-butanol or 2-amino-2-methyl-1-propanol diluted in the THF solvent, and the mixture was stirred for 20 to 25 hours to give amic acid salt. The resulting amic acid salt was filtered and dried. The dried amic acid salt was dissolved in acetic anhydride. The reaction solution was imidized by the addition of sodium acetate reacted at 100° C. to 120° C. for 20 to 30 hours, and then cooled to room temperature. After cooling, sodium acetate used as a catalyst was removed by a filter. In the filtrate from which sodium acetate had been removed, acetic anhydride was removed by rotary evaporator, and then the residue was recrystallized from ethanol, hexane or isopropyl alcohol to produce maleimide-based monomer of the formula (2).

In addition, the maleimide-based monomer of formula (2) according to the present invention may be prepared in accordance with any one of the following steps (h) to (n): (h) adding $K_2CO_3$, NaOH or TMAH aqueous solution to 2-maleimidethyl acetate of the step (a) to produce 2-maleimidyl ethanol; or (i) adding $K_2CO_3$, NaOH or TMAH aqueous solution to 3-maleimidepropyl acetate of the step (b) to produce 3-maleimidyl propanol; or (j) adding $K_2CO_3$, NaOH or TMAH aqueous solution to 1-maleimideisopropyl acetate of the step (c) to produce 1-maleimidyl isopropanol; or (k) adding $K_2CO_3$, NaOH or TMAH aqueous solution to 2-maleimidepropyl acetate of the step (d) to produce 2-maleimidyl propanol; or (1) adding $K_2CO_3$, NaOH or TMAH aqueous solution to 2-maleimidebutyl acetate of the step (e) to produce 2-maleimidyl-1-butanol; or (m) adding $K_2CO_3$, NaOH or TMAH aqueous solution to 4-maleimidebutyl acetate of the step (f) to produce 4-maleimidyl-1-butanol; or (n) adding $K_2CO_3$, NaOH or TMAH aqueous solution to 2-maleimide-2-methylpropyl acetate of the step (g) to produce 2-maleimidyl-2-methyl-1-propanol.

Specifically, 2-maleimidethyl acetate, 3-maleimidepropyl acetate, 1-maleimideisopropyl acetate, 2-maleimidepropyl acetate, 2- maleimide butyl acetate, 4-maleimidebutyl acetate or 2-maleimide- 2-methylpropyl acetate were dissolved in dimethylformamide or tetrahydrofuran. To the mixture was slowly added $K_2CO_3$, NaOH or TMAH aqueous solution and then stirred at about −70° C. to about 70° C. for 20 to 30 hours. After removing the solvent, the residue was recrystallized from ethanol, hexane or isopropyl alcohol to produce the maleimide-based monomer of the formula (2).

Among the alicyclic olefin-based monomers of the formulas (3) and (4) according to the present invention, 5-norbornene-2-carboxylic acid, t-butyl 5-norbornene-2-carboxylate, 2-hydroxyethyl 5-norbornene-2-carboxylate, t-butyl bicyclo [2,2,2]oct- 5-ene-2-carboxylate, 2-hydroxyethyl bicyclo[2,2,2]oct-5-ene-2- carboxylic acid, bicyclo[2,2,2]oct- 5-ene-carboxylic acid, and mixtures thereof are preferred.

The alicyclic olefin-based monomers of the formula (3) and (4) according to the present invention may be prepared in accordance with any one of the following steps (o) to (t): (o) reacting cyclopentadiene with acrylic acid to produce 5-norbornene-2-carboxylic acid; or (p) reacting cyclopentadiene with t-butyl acrylate to produce t-butyl 5-norbornene-2-carboxylate; or (q) reacting cyclopentadiene with 2-hydroxyethyl acrylate to produce 2-hydroxyethyl 5-norbornene-2-carboxylate; or (r) reacting cyclohexadiene with t-butyl acrylate produce t-butyl bicyclo[2,2,2]oct-5-ene-2-carboxylate; or (s) reacting cyclohexadiene with 2-hydroxyethyl acrylate to produce 2-hydroxyethyl bicyclo [2,2,2]oct-5-ene-2-carboxylate; or (t) reacting cyclohexadiene with acrylic acid to produce bicyclo[2,2,2]oct-5-ene-2-carboxylic acid.

Specifically, acrylic acid, t-butyl acrylate or 2-hydroxyethyl acrylate were dissolved with cyclopentadiene or cyclohexadiene in dimethylformamide or tetrahydrofuran solvent.

After reacting at from about −30° C. to about 100° C. for 4 to 24 hours, the solvent was removed by rotary evaporator. The residue was distilled under reduced pressure to obtain the alicyclic olefin-based monomers of the formulas (3) and (4).

The copolymer resin of the present invention, consisting of at least one maleimide-based monomer of formula (2) and/or maleic anhydride, together with at least one alicyclic olefin-based monomer of formulas (3) or (4), may be prepared in accordance with a conventional polymerization technique. For instance, the polymerization is carried out by a bulk polymerization or a solution polymerization in the presence of a polymerization initiator. The polymerization initiator includes benzoyl peroxide, 2,2-azobisisobutyronitrile (AIBN), acetyl peroxide, lauryl peroxide, or t-butyl peracetate. As a polymerization solvent, tetrahydrofuran, cyclohexanone, methylethylketone, benzene, toluene, dioxane, dimethylformamide alone or the combination, may be used. Preferably, the polymerization is carried out at a temperature of from about 60° C. to about 75° C. for 4 to 24 hours under a nitrogen or argon atmosphere.

A photoresist composition useful for formulating fine patterns of semiconductor devices may be obtained by mixing the novel photoresist copolymer of the present invention with a photoacid generator in a solvent in a conventional manner. For instance, a process for formulating the photoresist of the present invention comprises the following steps (1) to (3): (1) dissolving the copolymer resin as defined above in a solvent; (2) stirring the reaction product of the step (1) with a photoacid generator; and (3) filtering the reaction product of the step (2).

Specifically, the copolymer resin of the present invention is first dissolved in cyclohexanone to which is added a photoacid generator. Then, this solution is filtered with an ultra fine filter to obtain a photoresist solution. The filtering is carried out through 0.005 to 0.02 μm membrane filter.

The amount of the copolymer resin varies depending upon the solvent, the photoacid generator and lithography conditions. The copolymer resin is preferably used in an amount of from about 5 to about 40 a by weight based upon the weight of the organic solvent used. As the photoacid generator, triphenylsulfonium triflate, dibutylnaphtylsulfonium triflate, 2, 6-dimethylphenylsulfonate, bis(arylsulfonyl)-diazomethane, oximesulfonate, 1,2-diazonaphthoquinone-4-sulfonate, etc. may be used. Preferably, sulfonium or onium salt, and more preferably triphenylsulfonium triflate or dibutylnaphthylsulfonium triflate, is used. The photoacid generator is present in an amount of from about 0.1 to about 10% by weight based upon the weight of the copolymer resin. Suitable solvents include any conventional organic solvent, including for example methyl 3-methoxypropionate.

The resulting photoresist solution is spin-coated on a silicon wafer which is, then, soft-baked at a temperature of from about 80° C. to about 150° C. for 1 to 5 minutes in an oven or on a hot plate. The soft-baked wafer is exposed by a stepper which uses deep UV or vaccum UV light or an excimer laser as a light source. Thereafter, the wafer is subjected to post-baking at a temperature of from about 100° C. to about 200° C. An ultra fine positive resist image can be obtained by immersing the post-baked wafer in 2.38% TMAH aqueous solution for about 90 seconds.

As set forth above, the photoresist prepared from the novel copolymer of the present invention can be coated at a thickness of 1.0 μm or less by virtue of its high etch resistance, thermal resistance and adhesion, thereby obtaining satisfactory results in resolution and depth of focus.

The present invention will be more specifically explained by the following examples. However, it should be understood that the technical scope of the present invention will not be limited to those examples in any manner. In these examples, "g" means grams; "ml" means milliliters; "mol" means mole(s); "μm" means micrometer; "%" or "percent" means percent by weight unless otherwise indicated; "°C" means degrees Centigrade; "THF" means tetrahydrofuran; "DMF" means dimethylformamide; and "AIBN" means 2,2'-azobis isobutyronitrile.

EXAMPLE 1

Synthesis of 2-maleimidethyl acetate (5)

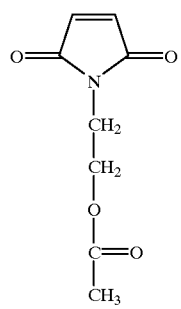

First, 1 mol of maleic anhydride was dissolved in 500 ml of purified THF solvent. To the mixture was slowly added 1 mol of ethanolamine diluted in the THF solvent (500 ml) and then stirred for 24 hours. The resulting amic acid salt was filtered and dried. Dried amic acid salt (100 g) was dissolved in 300 ml of acetic anhydride. The reaction solution was imidized by the addition of 3 g of sodium acetate reacted at 80° C. for 24 hours and then cooled to room temperature. After cooling, sodium acetate used as a catalyst, was removed by a filter. Residual acetic anhydride and acetic acid was removed by rotary evaporator, and the residue was recrystallized from isopropyl alcohol to obtain 40 g of pure 2-maleimidethyl acetate (yield: 40%). NMR spectral data of the thus obtained monomer (5) is shown in FIG. 1.

EXAMPLE 2

Synthesis of 3-maleimidepropyl acetate (6)

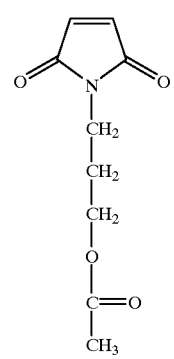

Maleic anhydride (1 mol) was dissolved in 500 ml of purified THF solvent. To the mixture was slowly added 1 mole of aminopropanol diluted in the THF solvent (500 ml) and then stirred for 24 hours. The resulting amic acid salt was filtered and dried. Dried amic acid salt (100 g) was dissolved in 100 ml of acetic anhydride. The reaction solution was imidized by the addition of 3 g of sodium acetate reacted at 80° C. for 24 hours, and then cooled to room temperature. After cooling, sodium acetate used as a catalyst, was removed by a filter. Residual acetic anhydride and acetic acid was removed by rotary evaporator, and the residue was recrystallized from isopropyl alcohol to obtain 41 g of pure 3-maleimidepropyl acetate (yield 41%).

EXAMPLE 3

Synthesis of 1-maleimideisopropyl acetate (7)

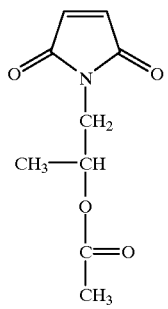

Maleic anhydride (1 mol) was dissolved in 500 ml of purified THF solvent. To the mixture was slowly added 1 mol of 1-amino-2-propanol diluted in the THF solvent (500 ml), and stirred for 24 hours. The resulting amic acid salt was filtered and dried. Dried amic acid salt (100 g) was dissolved in 250 ml of acetic anhydride. The reaction solution was imidized by the addition of 3 g of sodium acetate reacted at 80° C. for 24 hours, and then cooled to room temperature. After cooling, sodium acetate used as a catalyst, was removed by a filter residual acetic anhydride and acetic acid was removed by rotary evaporator, and then the residue was recrystallized from isopropyl alcohol to obtain 37 g of pure 1-maleimideisopropyl acetate (yield: 37%).

EXAMPLE 4

Synthesis of 2-maleimidepropyl acetate (8)

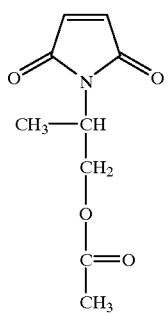

(8)

Maleic anhydride (1 mol) was dissolved in 500 ml of purified THF solvent. To the mixture was slowly added 1 mol of 2-amino-1-propanol diluted in the THF solvent (500 ml) and then stirred for 24 hours. The resulting amic acid salt was filtered and dried. Dried amic acid salt (100 g) was dissolved in 350 ml of acetic anhydride. The reaction solution was imidized by the addition of 3 g of sodium acetate reacted at 80° C. for 24 hours, and then cooled to room temperature. After cooling, sodium acetate used as a catalyst, was removed by a filter. Residual acetic anhydride was removed by rotary evaporator, and then the residue was recrystallized from isopropyl alcohol to obtain 37 g of pure 2-maleimidepropyl acetate (yield: 37%).

EXAMPLE 5

Synthesis of 2-maleimidebutyl acetate (9)

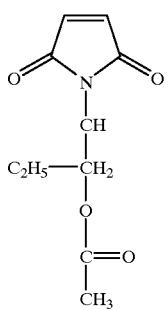

(9)

Maleic anhydride (1 mol) was dissolved in 500 ml of purified THF solvent. To the mixture was slowly added 1 mol of 2-amino-1-butanol diluted in the THF solvent (500 ml) and then stirred for 24 hours. The resulting amic acid salt was filtered and dried. Dried amic acid salt (100 g) was dissolved in 400 ml of acetic anhydride. The reaction solution was imidized by the addition of 3 g of sodium acetate reacted at 80° C. for 24 hours, and then cooled to room temperature. After cooling, sodium acetate used as a catalyst, was removed by a filter. Residual acetic anhydride and acetic acid was removed from the filtrate by rotary evaporator, and then the residue was recrystallized from isopropyl alcohol to obtain 43 g of pure 2-maleimidebutyl acetate (yield: 43%).

EXAMPLE 6

Synthesis of 4-maleimidebutyl acetate (10)

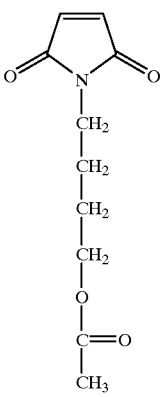

(10)

Maleic anhydride (1 mol) was dissolved in 500 ml of purified THF solvent. To the mixture was slowly added 1 mol of 4-amino-1-butanol diluted in the THF solvent (500 ml) and then stirred for 24 hours. The resulting amic acid salt was filtered and dried. Dried amic acid salt (100 g) was dissolved in 300 g of acetic anhydride. The reaction solution was imidized by the addition of 3 g of sodium acetate reacted at 80° C. for 24 hours, and then cooled to room temperature. After cooling, sodium acetate used as a catalyst, was removed by a filter. Residual acetic anhydride and acetic acid was removed from the filtrate by rotary evaporator, and then the residue was recrystallized from isopropyl alcohol to obtain 31 g of pure 4-maleimidebutyl acetate (yield: 31%).

EXAMPLE 7

Synthesis of 2-maleimide-2-methylpropyl acetate (11)

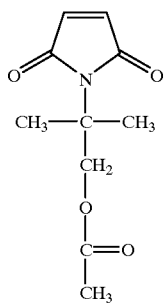

(11)

Maleic anhydride (100 g) was dissolved in 500 ml of purified THF solvent. To the mixture was slowly added 1 mole of 2-amino-2-methyl-1-propanol diluted in the THF solvent (500 ml) and then stirred for 24 hours. The resulting amic acid salt was filtered and dried. Dried amic acid salt (100 g) was dissolved in 300 ml of acetic anhydride. The reaction solution was imidized by the addition of 3 g of sodium acetate reacted at 80° C. for 24 hours, and then cooled to room temperature. After cooling, sodium acetate used as a catalyst, was removed by a filter. Residual acetic anhydride and acetic acid was removed from the filtrate by rotary evaporator, and then the residue was recrystallized from isopropyl alcohol to obtain 40 g of pure 2-maleimide-2-methylpropyl acetate (yield: 40%).

EXAMPLE 8

Synthesis of 2-maleimidylethanol (12)

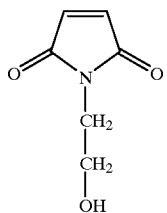

(12)

Maleimidethyl acetate (50 g) obtained from Example 1 was dissolved in 300 g of DMF solvent. To the mixture was slowly added 300 ml of 3% TMAH aqueous solution, and the solution was stirred at 25° C. for 24 hours. After removing the solvent, the residue was recrystallized from isopropyl alcohol to obtain 30 g of pure 2-maleimidyl ethanol (yield: 60%).

EXAMPLE 9

Synthesis of 3-maleimidylpropanol (13)

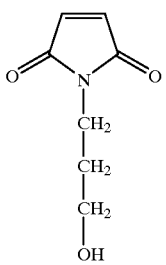

(13)

3-Maleimidepropyl acetate (50 g) obtained from Example 2 was dissolved in 300 g of DMF solvent. To the mixture was slowly added 300 ml of 3% TMAH aqueous solution, and the solution was stirred at 25° C. for 24 hours. After removing the solvent, the residue was recrystallized from isopropyl alcohol to obtain 28 g of pure 3-maleimidyl propanol (yield: 56%).

EXAMPLE 10

Synthesis of 1-maleimidylisopropanol (14)

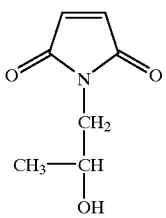

(14)

1-Maleimideisopropyl acetate (50 g) obtained from Example 3 was dissolved in 300 g of DMF solvent. To the mixture was slowly added 300 ml of 3% TMAH aqueous solution, and the solution was stirred at 25° C. for 24 hours. After removing the solvent, the residue was recrystallized from isopropyl alcohol to obtain 20 g of pure 1-maleimidylisopropanol (yield: 40%).

EXAMPLE 11

Synthesis of 2-maleimidylpropanol (15)

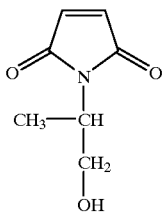

(15)

2-Maleimidepropyl acetate (50 g) obtained from Example 4 was dissolved in 300 g of DMF solvent. To the mixture was slowly added 300 ml of 3% TMAH aqueous solution, and the solution was stirred at 25° C. for 24 hours. After removing the solvent, the residue was recrystallized from isopropyl alcohol to obtain 41 g of pure 2-maleimidyl propanol (yield: 41%).

EXAMPLE 12

Synthesis of 2-maleimidyl-1-butanol (16)

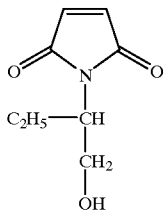

(16)

2-Maleimidebutyl acetate (50 g) obtained from Example 5 was dissolved in 300 g of DMF solvent. To the mixture was slowly added 300 ml of 3% TMAH aqueous solution, and the solution was stirred at 25° C. for 24 hours. After removing the solvent, the residue was recrystallized from isopropyl alcohol to obtain 20 g of pure 2-maleimidyl-1-butanol (yield: 40%).

EXAMPLE 13

Synthesis of 4-maleimidyl-1-butanol (17)

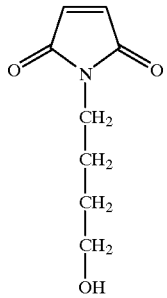

(17)

4-Maleimidebutyl acetate (50 g) obtained from Example 6 was dissolved in 300 g of DMF solvent. To the mixture was slowly added 300 ml of 3% TMAH aqueous solution, and the solution was stirred at 25° C. for 24 hours. After removing the solvent, the residue was recrystallized from isopropyl alcohol to obtain 22 g of pure 4-maleimidyl-1-butanol (yield: 44%).

EXAMPLE 14

Synthesis of 2-maleimidyl-2-methyl-1-propanol (18)

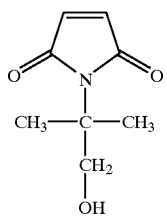

(18)

2-Maleimide-2-methylpropyl acetate (50 g) obtained from Example 7 was dissolved in 300 g of DMF solvent. To the mixture was slowly added 300 ml of 3% TMAH aqueous solution, and the solution was stirred at 25° C. for 24 hours. After removing the solvent, the residue was recrystallized from isopropyl alcohol to obtain 25 g of pure 2-maleimidyl-2-methyl-1-propanol (yield: 50%)

EXAMPLE 15

Synthesis of t-butyl 5-norbornene-2-carboxylate (19)

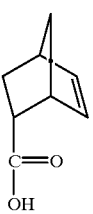

(19)

Figure 2:
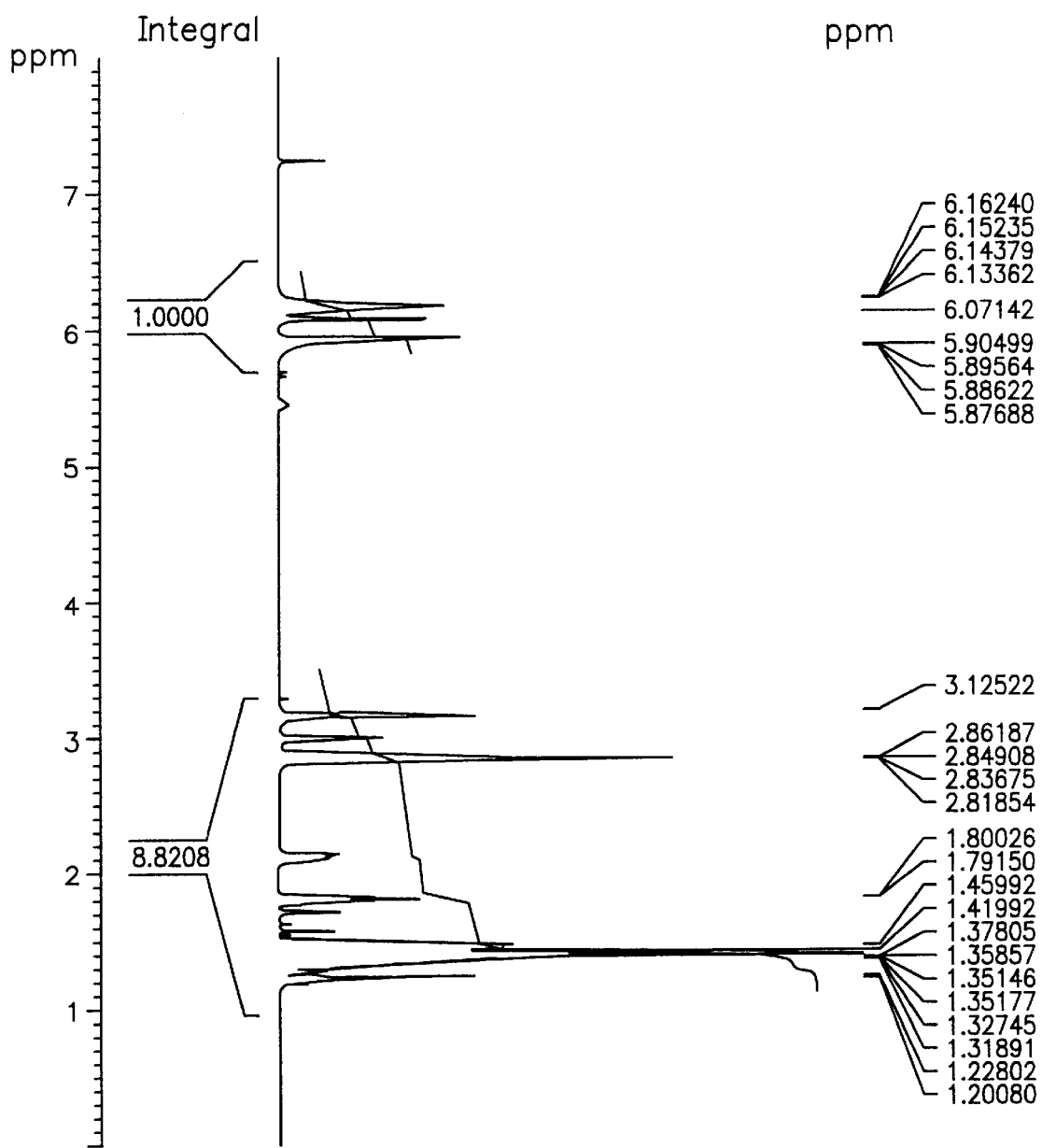
FIG. 2 is the NMR spectra of compound (19) obtained through the process of Example 15.

Cyclopentadiene (66 g) and 154 g of t-butyl acrylate were dissolved in 500 g of THF solvent. After the reaction at 30° C. for 24 hours, the solvent and excess t-butyl acrylate were removed in rotary evaporator. The residue was distilled under reduced pressure to obtain 150 g of t-butyl 5-norbornene- 2-carboxylate as a mixture of endo and exo (yield: 68%). NMR spectral data of the resulting compound (19) is shown in FIG. 2.

EXAMPLE 16

Synthesis of 5-norbornene-2-carboxylic acid (20)

(20)

Figure 3:
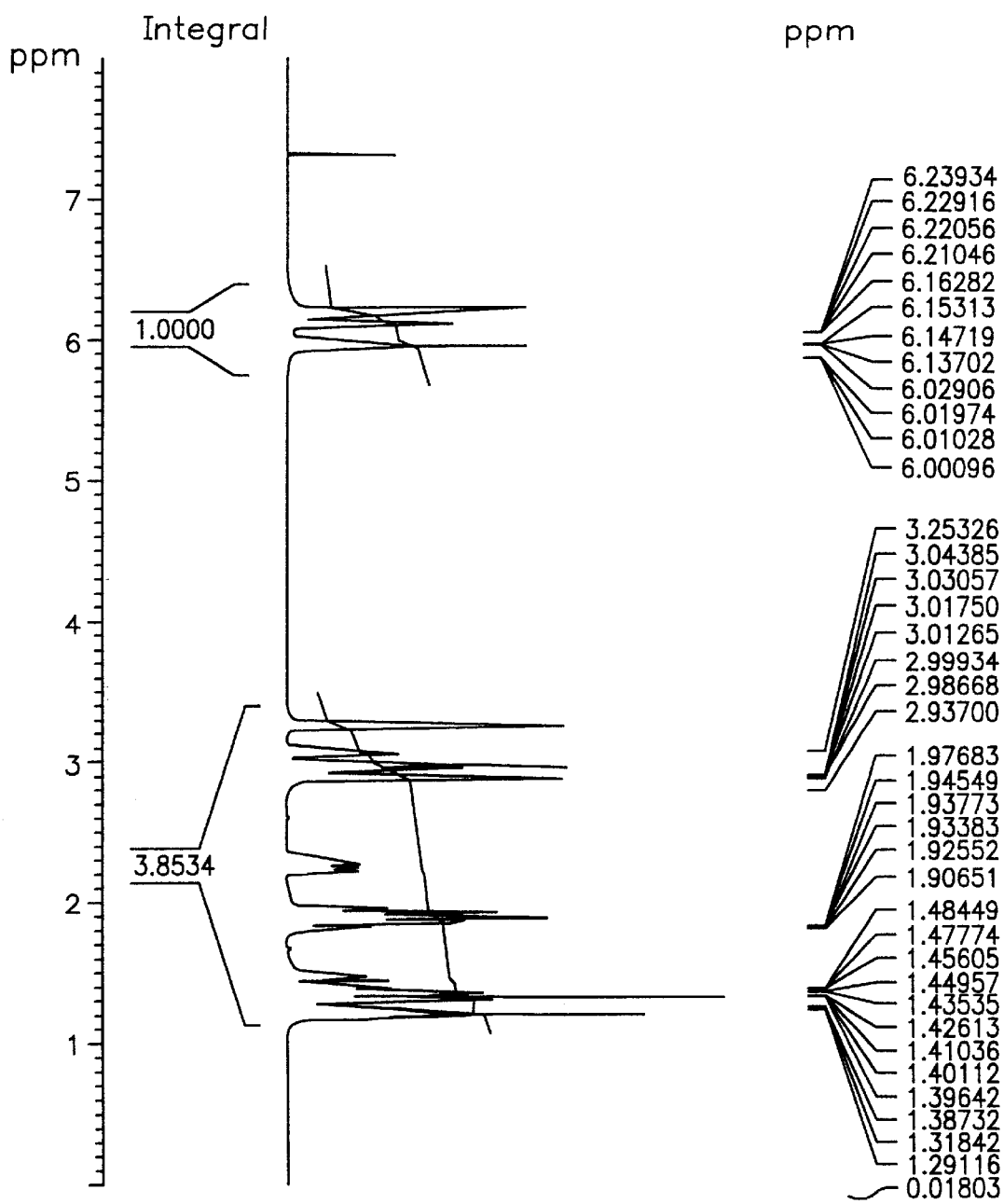
FIG. 3 is the NMR spectra of compound (20) obtained through the process of Example 16.

Cyclopentadiene (66 g) and 86 g of acrylic acid were dissolved in 500 g of THF solvent. After the reaction at 30° C. for 24 hours, the solvent and excess acrylic acid were removed by rotary evaporator. The residue was distilled under reduced pressure to obtain 110 g of 5-norbornene-2-carboxylic acid as a mixture of endo and exo (yield: 71%). NMR spectral data of the resulting compound (20) is shown in FIG. 3.

EXAMPLE 17

Synthesis of 2-hydroxyethyl 5-norbornene-2-carboxylate (21)

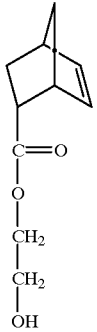

(21)

Figure 4:
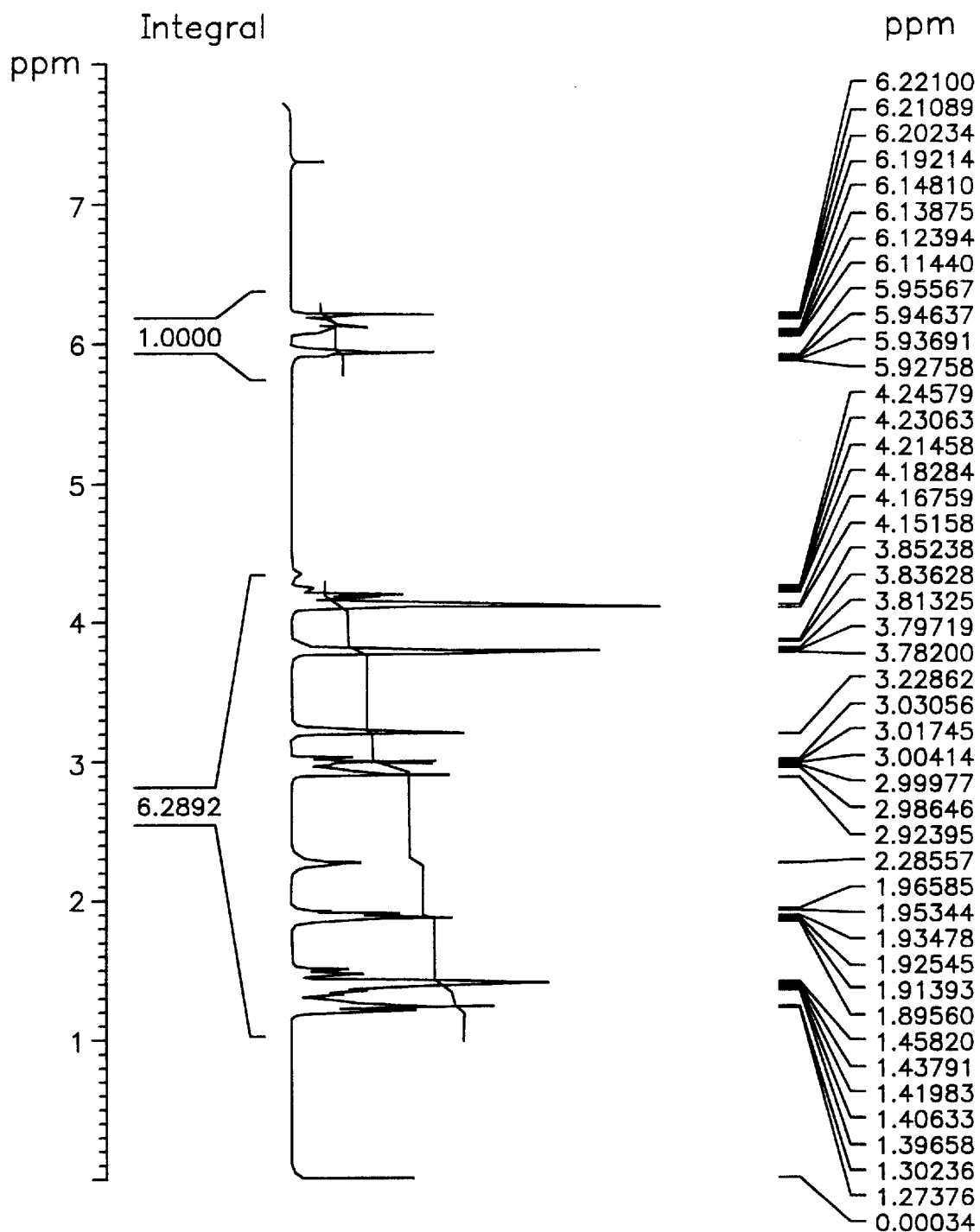
FIG. 4 is the NMR spectra of compound (21) obtained through the process of Example 17.
Figure 5:
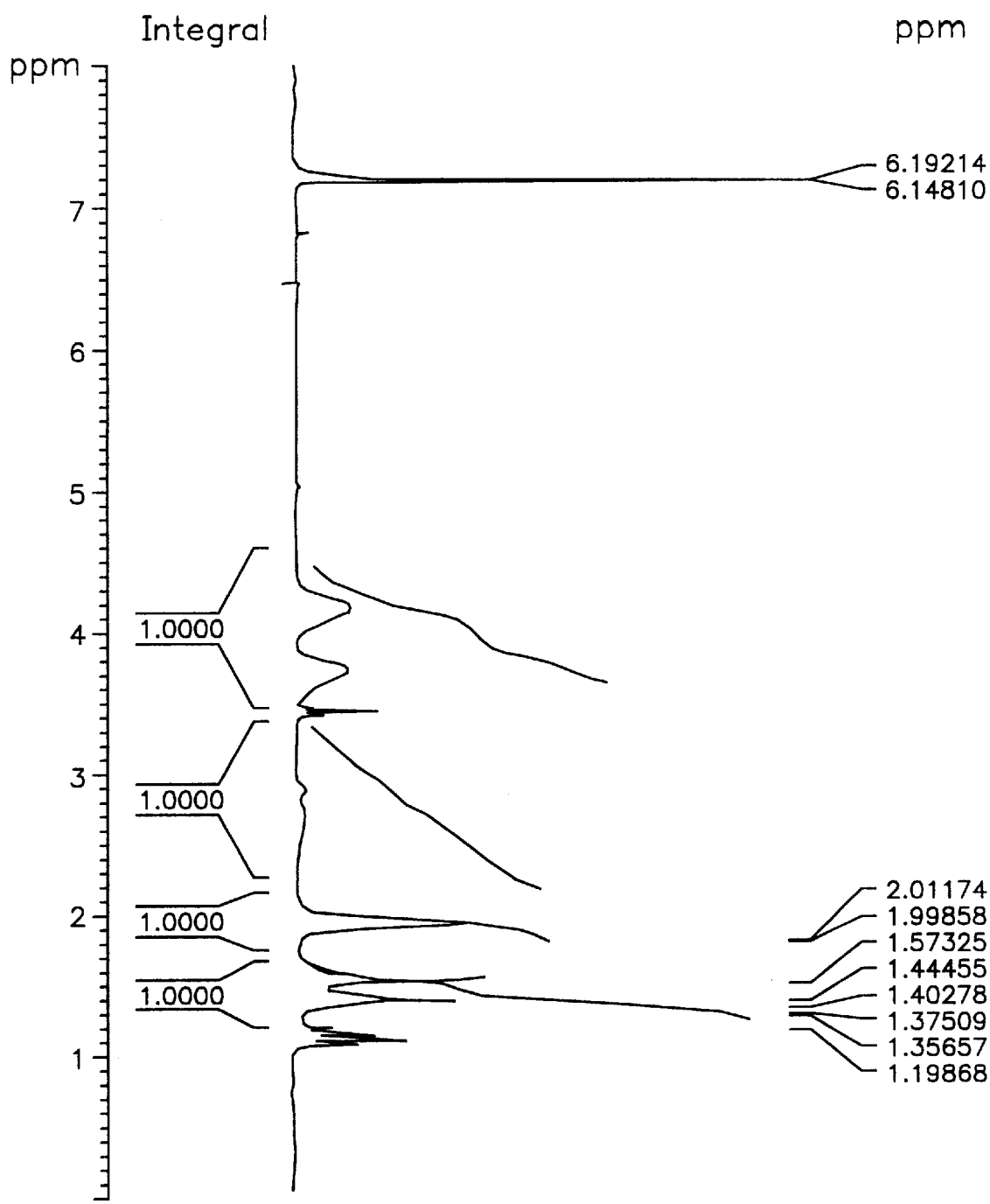
FIG. 5 is the NMR spectra of resin obtained through the process of Example 25.

Cyclopentadiene (66 g) and 140 g of 2-hydroxyethyl acrylate were dissolved in 500 g of THF solvent. After the reaction at 30° C. for 24 hours, the solvent was removed by rotary evaporator. The residue was distilled under reduced pressure to obtain 148 g of 2-hydroxyethyl 5-norbornene-carboxylate as a mixture of endo and exo (yield: 72%). NMR spectral data of the resulting compound (21) is shown in FIG. 4.

EXAMPLE 18

Synthesis of t-butyl bicyclo[2,2,2]oct-5-ene-2-carboxylate (22)

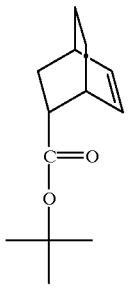

(22)

Cyclohexadiene (80g) and 154 g of t-butyl acrylate were dissolved in 500 g of THF solvent. After reacting at 50° C. for 24 hours, the solvent was removed by rotary evaporator. The residue was distilled under reduced pressure to obtain 112 g of t-butyl bicyclo[2,2,2]oct-5-ene-2-carboxylate as a mixture of endo and exo (yield: 48%).

EXAMPLE 19

Synthesis of 2-hydroxyethyl bicyclo[2,2,2]oct-5-ene-2-carboxylate (23)

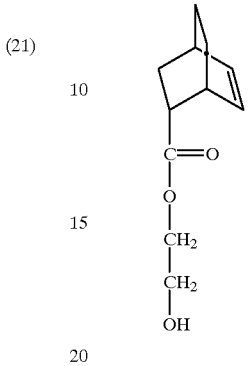

(23)

Cyclohexadiene (80 g) and 140 g of 2-hydroxyethyl acrylate were dissolved in 500 g of THF solvent. After reacting at 50° C. for 24 hours, the solvent was removed by rotary evaporator. The residue was distilled under reduced pressure to obtain 100 g of 2-hydroxyethyl bicyclo[2,2,2]oct-5-ene-2- carboxylate as a mixture of endo and exo (yield: 45%).

EXAMPLE 20

Synthesis of bicyclo[2,2,2]oct-5-ene-2-carboxylate (24)

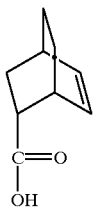

(24)

Cyclohexadiene (80 g) and 86 g of acrylic acid were dissolved in 500 g of THF solvent. After reacting at 50° C. for 48 hours, the solvent was removed by rotary evaporator. The residue was distilled under reduced pressure to obtain 83 g of bicyclo[2,2,2]oct-5-ene-2-carboxylate as a mixture of endo and exo (yield: 50%).

EXAMPLE 21

Synthesis of poly[2-maleimidylethanol/t-butyl 5-norbornene-2-carboxylate/2-hydroxyethyl 5-norbornene-2-carboxylate/5-norbornene-2-carboxylic acid] copolymer resin 2-Maleimidylethanol (12) (0.5 to 1 mol), 0.1 to 1 mol of t-butyl 5-norbornene-2-carboxylate (19), 0.05 to 1 mol of 2-hydroxyethyl 5-norbornene-2-carboxylate (21), and 0.01 to 0.3 mol of 5-norbornene-2-carboxylic acid (20) were dissolved in 150 to 250 g of THF solvent to which was added 0.5 to 20 g of AIEN as a polymerization initiator. The reaction mixture was allowed to react at 60° C. to 75° C. for 4 to 24 hours under an argon atmosphere. The resulting crude resin was precipitated with ethyl ether and dried to obtain poly[2-maleimidylethanol/t-butyl 5-norbornene-2-carboxylate/2-hydroxyethyl-5-norbornene-2-carboxylate/5-norbornene-2-carboxylic acid] copolymer resin.

EXAMPLE 22

Synthesis of poly[3-maleimidylpropanol/t-butyl 5-norbornene-2-carboxylate/2-hydroxyethyl 5-norbornene-2-carboxylate/5-norbornene-2-carboxylic acid] copolymer resin 3-Maleimidylpropanol (13) (0.5 to 1 mol), 0.1 to 1 mol of t-butyl 5-norbornene-2-carboxylate (19), 005 to 1 mol of 2-hydroxy ethyl-5-norbornene- 2-carboxylate (21), and 0.01 to 0.3 mol of 5-norbornene-2-carboxylic acid (20) were dissolved in 150 to 250 g of THF to which was added 0.5 to 20 g of AIBN as a polymerization initiator. The reaction mixture was allowed to react at 60° C. to 75° C. for 4 to 24 hours under an argon atmosphere. The resulting crude resin was precipitated with hexane and dried to obtain poly[3-maleimidylpropanol/t-butyl-5-norbornene-2-carboxylate/2-hydroxyethy-15-norbornene ne-2-carboxylate/5-norbornene-2-carboxylic acid] copolymer resin.

EXAMPLE 23

Figure 6:
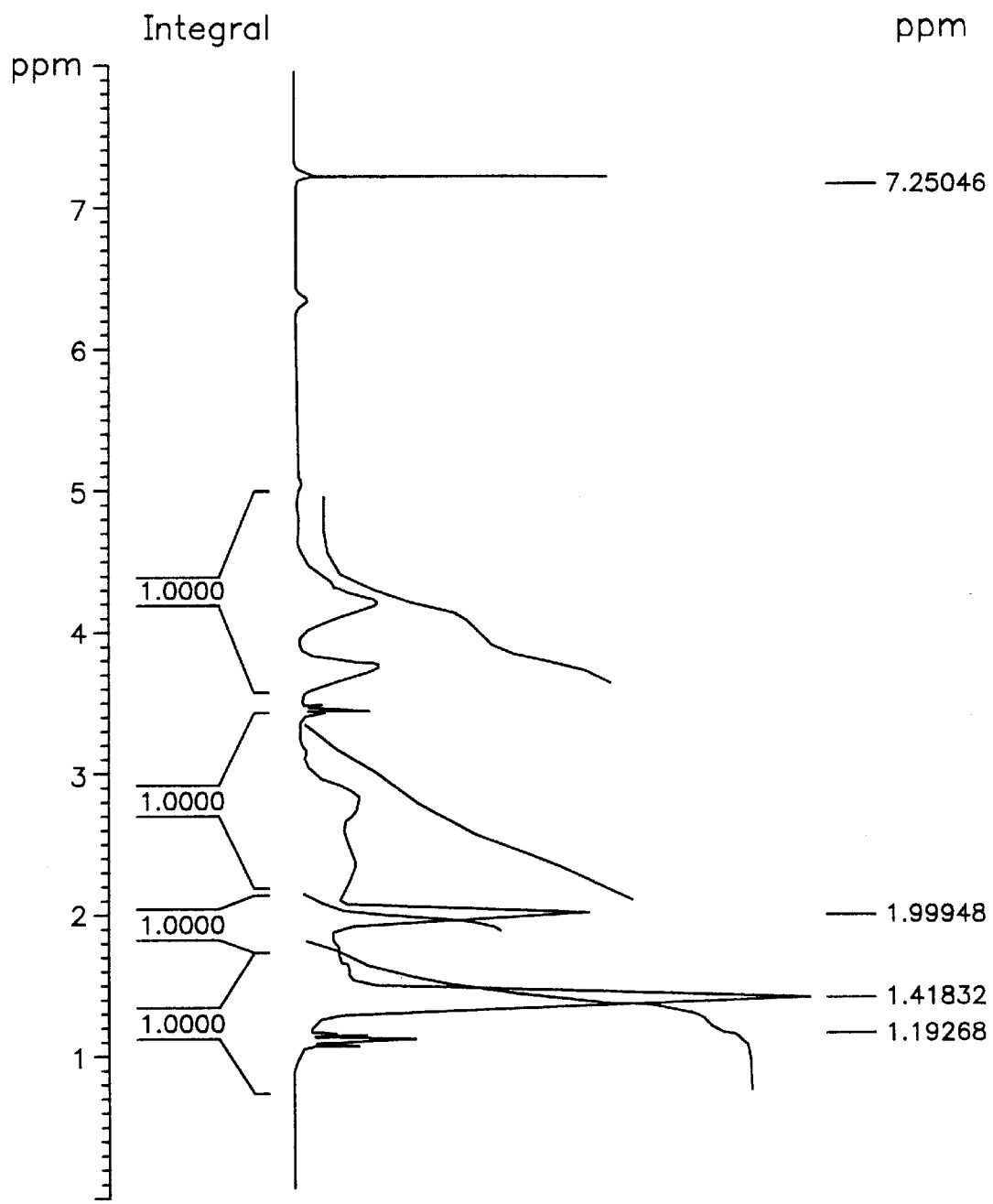
FIG. 6 is the NMR spectra of resin obtained through the process of Example 23.

Synthesis of poly[2-maleimidylethanol/maleic anhydride/t-butyl 5-norbornene-2- carboxylate/2-hydroxyethyl 5-norbornene-2-carboxylate/5-norbornene-2-carboxylic acid] copolymer resin 2-Maleimidylethanol (12) (0.3 to 1 mol), 0.05 to 1 mol of maleic anhydride, 0.1 to 1 mol of t-butyl 5-norbornene-2-carboxylate (19), 0.05 to 1 mol of 2-hydroxyethyl 5-norbornene-2-carboxylate (21), and 0.01 to 0.3 mol of 5-norbornene-2-carboxylic acid (20) were dissolved in 180 to 230 g of THF to which was added 0.5 to 20 g of AIBN as a polymerization initiator. The reaction mixture was allowed to react at 60° C. to 75° C. for 4 to 24 hours under a nitrogen atmosphere. The resulting crude resin was precipitated with ethyl ether and dried to obtain poly[2-maleimidylethanol/maleic anhydride/t-butyl 5-norbornene-2-carboxylate/2-hydroxyethyl 5-norbornene-2-carboxylate/5-norbornene-2-carboxylic acid] copolymer resin. The NMR spectral data of the resulting resin is shown in FIG. 6.

EXAMPLE 24

Synthesis of poly[3-maleimidylpropanol/maleic anhydride/t-butyl 5-norbornene-2- carboxylate/2-hydroxyethyl 5-norbornene-2-carboxylate/5-norbornene-2-carboxylic acid] copolymer resin 3-Maleimidylpropanol (13) (0.3 to 1 mol), 0.05 to 1 mol of maleic anhydride, 0.1 to 1 mol of t-butyl 5-norbornene-2-carboxylate (19), 0.05 to 1 mol of 2-hydroxyethyl 5-norbornene-2-carboxylate (21), and 0.01 to 0.3 mol of 5-norbornene-2-carboxylic acid (20) were dissolved in 150 to 250 g of THF to which was added 0.5 to 20 g of AIBN as a polymerization initiator. The reaction mixture was allowed to react at 60° C. to 75° C. for 4 to 24 hours under an argon atmosphere. The resulting crude resin was precipitated with hexane and dried to obtain poly[3-maleimidylpropanol/maleic anhydride/t-butyl-5-norbornene-2- carboxylate/2-hydroxyethyl 5- norbornene-2-carboxylate/5-norbornene-2-carboxylic acid] copolymer resin.

EXAMPLE 25

Synthesis of poly[2-maleimidethyl acetate/t-butyl 5-norbornene-2-carboxylate/2- hydroxyethyl 5-norbornene-2-carboxylate/5-norbornene-2-carboxylic acid] copolymer resin 2-Maleimidethyl acetate (5) (0.5 to 1 mol), 0.1 to 1 mol of t-butyl 5-norbornene-2-carboxylate (19), 0.05 to 1 mol of 2-hydroxy ethyl-5-norbornene-2- carboxylate (21), and 0.1 to 0.3 mol of 5-norbornene-2-carboxylic acid (20) were dissolved in 200 to 270 g of THF to which was added 0.5 to 20 g of AIBN as a polymerization initiator. The reaction mixture was allowed to react at 60° C. to 75° C. for 4 to 24 hours under a nitrogen atmosphere. The resulting crude resin was precipitated with ethyl ether and dried to obtain poly [2-maleimidethyl acetate/t-butyl 5-norbornene-2-carboxylate/ 2-hydroxyethyl 5-norbornene-2-carboxylate/5-norbornene-2-carboxylic acid] copolymer resin.

EXAMPLE 26

Synthesis of poly[3-maleimidepropyl acetate/5-norbornene-2-carboxylate/2-hydroxyethyl 5-norbornene-2-carboxylate/5-norbornene-2-carboxylic acid] copolymer resin 3-Maleimidepropyl acetate (6) (0.5 to 1 mol), 0.01 to 1 mol of t-butyl-5-norbornene-2-carboxylate (19), 0.05 to 1 mol of 2-hydroxy ethyl 5-norbornene-2-carboxylate (21), and 0.01 to 0.3 mol of 5-norbornene-2-carboxylic acid (20) were dissolved in 240 to 290 g of THE solvent to which was added 0.5 to 20 g of AIBN as a polymerization initiator. The reaction mixture was allowed to react at 60° C. to 75° C. for 4 to 24 hours under an argon atmosphere. The resulting crude resin was precipitated with hexane and dried to obtain poly[3-maleimidepropyl acetate/5-norbornene-2-carboxylate/ 2-hydroxyethyl 5-norbornene-2-carboxylate/5-norbornene-2-carboxylic acid] copolymer resin.

EXAMPLE 27

Photoresist

The copolymer resin (10 g) obtained from Example 21 was dissolved in 40 g of methyl 3-methoxy propionate solvent to which a photoacid generator, triphenylsulfonium triflate, was added in the amount of 0.01 to 1 g, corresponding to 0.1 to 10% by weight of the copolymer resin used. The reaction mixture was stirred and then filtered through 0.10 $\mu$m filter to obtain a photoresist solution. The photoresist solution was spin-coated on a wafer and then soft-baked at a temperature of 110° C. for 90 seconds in an oven. The soft-baked wafer was exposed in an ArF excimer laser stepper which was then subjected to post-baking at a temperature of 110° C. for 90 seconds. The post-baked wafer was immersed in 2.38% TMAH developer solution to formulate 0.13 $\mu$m L/S pattern.

EXAMPLE 28

Photoresist

The photoresist pattern was formulated in the same manner as Example 27 except that 10 g of the copolymer resin obtained from Example 22 was used as a photoresist resin and 0.01 to 1 g of dibutylnaphthylsulfonium triflate was added as a photoacid generator.

EXAMPLE 29

Photoresist

The photoresist pattern was formulated in the same manner as Example 27 provided that 10 g of the copolymer resin obtained from Example 23 was used as a photoresist resin and 0.01 to 1 g of dibutylnaphthyl sulfonium triflate was added as a photoacid generator.

EXAMPLE 30

Photoresist

The photoresist pattern was formulated in the same manner as Example 27 except that 10 g of the copolymer resin obtained from Example 24 was used as a photoresist resin and 0.01 to 1 g of triphenylsulfonium triflate was added as a photoacid generator.

EXAMPLE 31

Photoresist

The photoresist pattern was formulated in the same manner as Example 27 except that 10 g of the copolymer resin obtained from Example 25 was used as a photoresist resin and 0.01 to 1 g of dibutylnaphthyl sulfonium triflate was added as a photoacid generator.

EXAMPLE 32

Photoresist

The photoresist pattern was formulated in the same manner as Example 27 except that 10 g of the copolymer resin obtained from Example 26 was used as a photoresist resin and 0.01 to 1 g of triphenylsulfonium triflate was added as a photoacid generator.

The maleimide-introduced copolymer resin for photoresist according to the present invention can easily be copolymerized with an alicyclic olef in unit, has a physical property capable of enduring in 2.38% TMAH developer, and increases adhesion of ArF or KrF photoresist. The photoresist film using the copolymer resin according to the present invention can be applied to highly integrate semiconductor devices.

Although the invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention. The invention is defined by the following claims, with equivalents of the claims to be included therein.

That which is claimed is:

1. A process for preparing the maleimide-based monomer of formula (2):

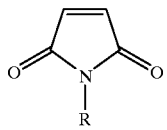

(2)

wherein R is selected from the group consisting of main or side chain-substituted alkyls having 1 to 10 carbon atoms, main or side chain-substituted primary, secondary and tertiary alcohols having 1 to 10 carbon atoms, and main or side chain-substituted diols having 1 to 10 carbon atoms;

said process comprising reacting $K_2CO_3$ and, NaOH or tetramethyl ammonium hydroxide aqueous solution with an acetate reactant selected from the group consisting of 2-maleimidethyl acetate, 3-maleimidepropyl acetate, 1-maleimideisopropyl acetate, 2-maleimidepropyl acetate, 2-maleimidebutyl acetate, 4-maleimidebutyl acetate, and 2-maleimide-2-methylpropyl acetate to produce the maleimide-based monomers of formula (2).

2. A copolymer resin for use in KrF or ArF photoresists comprising at least one maleimide-based monomer of formula (2):

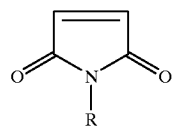

(2)

wherein R is selected from the group consisting of main or side chain-substituted alkyl acetates having 2 to 4 carbon atoms in the alkyl moiety, main or side chain-substituted primary, secondary and tertiary alcohols having 1 to 10 carbon atoms, and main or side chain-substituted diols having 1 to 10 carbon atoms; and at least one alicyclic olefin-based monomer of the formula (3):

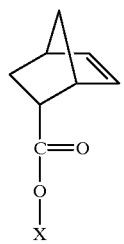

wherein X is selected from the group consisting of hydrogen, t-butyl and 2-hydroxyethyl.

3. The copolymer resin of claim 2, wherein the maleimide-based monomer is selected from the group consisting of 2-maleimidethyl acetate, 3-maleimidepropyl acetate, 1-maleimideisopropyl acetate, 2-maleimidepropyl acetate, 2-maleimidebutyl acetate, 4-maleimidebutyl acetate, 2-maleimide-2-methyl propyl acetate, 2-maleimidyl ethanol, 3-maleimidyl propanol, 2-maleimidyl propanol, 1-maleimidylisopropanol, 2-maleimidyl-1-butanol, 4-maleimidyl-1-butanol and 2-maleimidyl-2-methyl-1-propanol.

4. The copolymer resin of claim 2, wherein the alicyclic olefin-based monomer is selected from the group consisting of 5-norbornene-2-carboxylic acid, t-butyl 5-norbornene-2-carboxylate, 2-hydroxyethyl-5-norbornene-2-carboxylate, t-butyl bicyclo[2,2,2] oct-5-ene-2-carboxylate, 2-hydroxyethyl bicyclo[2,2,2]oct-5-ene-2-carboxylate acid and bicyclo[2,2,2]oct-5-ene-carboxylic acid.

5. The copolymer resin of claim 2, said copolymer further comprising maleic anhydride.

6. A process for preparing the copolymer resin as defined in claim 3 which comprises polymerizing at least one maleimide-based monomer of formula (2) with at least one alicyclic olefin-based monomer of formula (3)

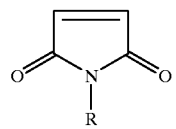

(2)

wherein R is selected from the group consisting of main or side chain-substituted alkyl acetates having 2 to 4 carbon atoms in the alkyl moiety, main or side chain-substituted primary, secondary and tertiary alcohols having 1 to 10 carbon atoms, and main or side chain-substituted diols having 1 to 10 carbon atoms;

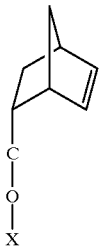

(3)

wherein X is selected from the group consisting of hydrogen, t-butyl and 2-hydroxyethyl in the presence of a polymerization initiator.

7. The process of claim 6, wherein the maleimide-based monomer is selected from the group consisting of 2-maleimidethyl acetate, 3-maleimidepropyl acetate, 1-maleimideisopropyl acetate, 2-maleimide propyl acetate, 2-maleimidebutyl acetate, 4-maleimidebutyl acetate, 2-maleimide-2-methyl propyl acetate, 2-maleimidyl ethanol, 3-maleimidyl propanol, 2-maleimidyl propanol, 1-maleimidylisopropanol, 2-maleimidyl-1-butanol, 4-maleimidyl-1-butanol and 2-maleimidyl-2-methyl-1-propanol.

8. The process of claim 6, wherein the alicyclic olefin-based monomer is selected from the group consisting of 5-norbornene-2- carboxylic acid, t-butyl 5-norbornene-2-carboxylate, 2-hydroxyethyl 5-norbornene-2-carboxylate, t-butyl bicyclo[2,2,2]oct-5-ene-2-carboxylate, 2-hydroxyethyl bicyclo[2,2,2]oct-5- ene-2-carboxylate and bicyclo[2,2,2]oct-5-ene-carboxylic acid.

9. The process of claim 6, wherein the polymerization is initiated by 2,2'-azobisisobutyronitrile.

10. The process of claim 6, wherein the polymerization is carried out at a temperature of 60° C. to 75° C. for 4 to 24 hours under a nitrogen or argon atmosphere.

11. The process of claim 6, further comprising adding maleic anhydride to the polymerizing step to make said maleimide-based monomer and said alicyclic olef in-based monomer copolymerized with said maleic anhydride.

12. A process for preparing a poly[2-maleimidylethanol/ t-butyl 5-norbornene-2-carboxylate/2-hydroxyethyl 5-norbornene-2-carboxylate/5-norbornene-2-carboxylic acid] copolymer resin, said process comprising the steps:

(i) dissolving about 0.5 to about 1 mol of 2-maleimidylethanol, about 0.1 to about 1 mol of t-butyl 5-norbornene-2-carboxylate, about 0.05 to about 1 mol of 2-hydroxyethyl 5-norbornene-2-carboxylate and about 0.01 to about 0.3 mol of 5-norbornene-2-carboxylic acid with 150 to 250 g of tetrahydrofuran solvent;

(ii) adding about 0.5 to about 20 g of 2,2'-azobisisobutyronitrile as a polymerization initiator to the resultant solution of the step (i);

(iii) laying the resultant solution obtained from the step (ii) for a period of 4 to about 24 hours at a temperature of about 60° C. to about 75° C. under nitrogen atmosphere; and (iv) precipitating and drying the reaction product of the step (iii) to produce said copolymer resin.

13. A process for preparing a poly[3-maleimidylpropanol/ t-butyl-5-norbonen-2-carboxylate/2- hydroxyethyl 5-norbornene-2-carboxylate /5-norbornene-2-carboxylic acid] copolymer resin, said process comprising the steps:

(i) dissolving about 0.5 to about 1 mol of 3-maleimidylpropanol, about 0.1 to about 1 mol of t-butyl 5-norbornene-2-carboxylate, about 0.05 to about 1 mol of 2-hydroxyethyl 5-norbornene-2-carboxylate and about 0.01 to about 0.3 mol of 5-norbornene-2-carboxylic acid with 150 to 250 g of tetrahydrofuran solvent;

(ii) adding about 0.5 to about 20 g of 2,2'-azobisisobutyronitrile as a polymerization initiator to the resultant solution of the step (i);

(iii) laying the resultant solution of the step (ii) for a period of from 4 to about 24 hours at a temperature of from about 60° C. to about 75° C. under argon atmosphere; and (iv) precipitating and drying the product of the step (iii) to produce said copolymer resin.

14. A process for preparing a poly[2-maleimidylethanol/ maleic anhydride/ t-butyl 5-norbornene-2-carboxylate/2-hydroxyethy-15-norbornene-2-carboxylate/ 5-norbornene-2-carboxylic acid] copolymer resin, said process comprising the steps:

(i) dissolving from about 0.3 to about 1 mole of 2-maleimidylethanol, from about 0.05 to about 1 mol of maleic anhydride, from about 0.1 to about 1 mol of t-butyl 5-norbornene-2-carboxylate, from about 0.05 to about 1 mol of 2-hydroxyethyl 5-norbornene-2-carboxylate and from about 0.01 to about 0.3 mol of 5-norbornene-2-carboxylic acid with from 180 to 230 g of tetrahydrofuran solvent;

(ii) adding from about 0.5 to about 20 g of 2,2'-azobisisobutyronitrile as a polymerization initiator to the resultant solution of the step (i);

(iii) laying the resultant solution of the step (ii) for a period of from 4 to about 24 hours at a temperature of from about 60° C. to about 75° C. under nitrogen atmosphere; and (iv) precipitating and drying the product of the step (iii) to produce said copolymer resin.

15. A process for preparing a poly[3-maleimidyl propanol/maleic anhydride/t-butyl 5-norbornene-2-carboxylate/2-hydroxyethyl 5-norbornene-2-carboxylate/5-norbornene-2-carboxylic acid] copolymer resin, said process comprising the steps:

(i) dissolving from about 0.3 to about 1 mol of 3-maleimidylpropanol, from about 0.05 to about 1 mole of maleic anhydride, from about 0.1 to about 1 mol of t-butyl 5-norbornene-2-carboxylate, from about 0.05 to about 1 mol of 2-hydroxyethyl 5-norbornene-2-carboxylate and from about 0.01 to about 0.3 mol of 5-norbornene-2-carboxylic acid with from 150 to 250 g of tetrahydrofuran solvent;

(ii) adding from about 0.5 to about 20 g of 2,2'-azobisisobutyronitrile as a polymerization initiator to the resultant solution of the step (i);

(iii) laying the resultant solution of the step (ii) for a period of from 4 to about 24 hours at a temperature of from about 60° C. to about 75° C. under nitrogen atmosphere; and (iv) precipitating and drying the product of the step (iii) to produce said copolymer resin.

16. A process for preparing a poly[2-maleimidyl ethyl acetate/t-butyl-5- norbornene-2-carboxylate/2-hydroxyethyl 5-norbornene-2-carboxylate /5-norbornene-2-carboxylic acid] copolymer resin, said process comprising the steps:

(i) dissolving from about 0.5 to about 1 mol of 2-maleimidylethyl acetate, from about 0.1 to about 1 mol of t-butyl 5-norbornene-2-carboxylate, from about 0.05 to about 1 mol of 2-hydroxyethyl-5-norbornene-2-carboxylate and from about 0.01 to about 0.3 mol of 5-norbornene-2-carboxylic acid with 200 to about 270 g of tetrahydrofuran solvent;

(ii) adding from about 0.5 to about 20 g of 2,2'-azobisisobutyronitrile as a polymerization initiator to the resultant solution of the step (i);

(iii) laying the resultant solution of the step (ii) for a period of from 4 to about 24 hours at a temperature of from about 60° C. to about 750° 1 C. under nitrogen atmosphere; and (iv) precipitating and drying the product of the step (iii) to produce said copolymer resin.

17. A process for preparing a poly[3-maleimidepropyl 2 acetate/t-butyl 5- norbornene-2-carboxylate/2-hydroxyethyl 5-norbornene-2-carboxylate/ 5-norbornene-2-carboxylic acid] copolymer resin, said process comprising the steps:

(i) dissolving from about 0.5 to about 1 mol of 3-maleimidepropyl acetate, from about 0.1 to about 1 mol of t-butyl 5-norbornene-2-carboxylate, from about 0.05 to about 1 mol of 2-hydroxyethyl 5-norbornene-2-carboxylate and from about 0.01 to about 0.3 mole of 5-norbornene-2-carboxylic acid with from 240 to 290 g of tetrahydrofuran solvent;

(ii) adding from about 0.5 to about 20 g of 2,2'-azobisisobutyronitrile as a polymerization initiator to the resultant solution of the step (i);

(iii) laying the resultant solution of the step (ii) for a period of from 4 to about 24 hours at a temperature of from about 60° 0C. to about 75° C. under nitrogen or argon atmosphere; and (iv) precipitating and drying the product of the step (iii) to produce said copolymer resin.

18. A photoresist comprising the copolymer resin of claim 2, a photoacid generator and a solvent.

19. The photoresist of claim 18, wherein the solvent is 3-methoxymethyl propionate.

20. The photoresist of claim 18, wherein the photoacid generator is sulfonium salt or onium salt.

21. The photoresist of claim 20, wherein the photoacid generator is triphenylsulfonium triflate or dibutylnaphthyl-sulfonium triflate.

22. The photoresist of claim 18, wherein the copolymer resin is present in an amount of from about 5 to about 40% by weight with respect to the total weight of the solvent.

23. The photoresist of claim 18, wherein the photoacid generator is present in an amount of from about 0.1 to about 10% by weight with respect to the total weight of the copolymer resin.

24. A process for preparing a photoresist, said process comprising the steps:

(i) dissolving a copolymer resin consisting of at least one maleimide-based monomer of formula (2), maleic anhydride, and at least one alicyclic olefin-based monomer of the formula (3) or (4) with a solvent:

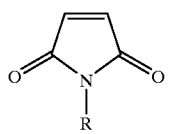
(2)

wherein R is selected from the group consisting of main or side chain-substituted alkyls having 1 to 10 carbon atoms, main or side chain-substituted primary, secondary and tertiary alcohols having 1 to 10 carbon atoms, and main or side chain-substituted diols having 1 to 10 carbon atoms;

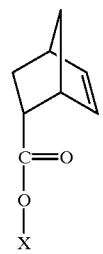
(3)

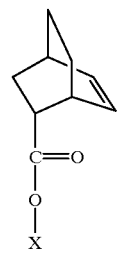
(4)

wherein X is selected from the group consisting of hydrogen, t-butyl and 2-hydroxyethyl;

(ii) stirring the resultant product of the step (i) with photo acid generator; and (iii) filtering the resultant product of the step (ii).

25. The process of claim 24, wherein the solvent is 3-methoxymethyl propionate.

26. The process of claim 24, wherein the copolymer resin is present in an amount of from about 5 to about 40% by weight with respect to the total weight of the solvent.

27. The process of claim 24, wherein the photoacid generator is sulfonium salt or onium salt.

28. The process of claim 24, wherein the photoacid generator is triphenyl sulfonium triflate or dibutylnaphthyl sulfonium triflate.

29. The process of claim 24, wherein the photoacid generator is present in an amount of from about 0.1 to about 10% by weight with respect to the total weight of the copolymer resin.

30. The process of claim 24, wherein said step (ii) of filtering is conducted using 0.005 to 0.02 μm membrane filter.

31. A semiconductor device comprising the photoresist of claim 18.

* * * * *

UNITED STATES PATENT AND TRADEMARK OFFICE
CERTIFICATE OF CORRECTION

PATENT NO. : 6,165,672
DATED : December 26, 2000
INVENTOR(S) : Jae Chang Jung; Keun Kyu Kong; Cheol Kyu Bok; Ki Ho Baik It is certified that error appears in the above-identified patent and that said Letters Patent is hereby corrected as shown below:

Column 2,
Lines 49-60, delete the following formula

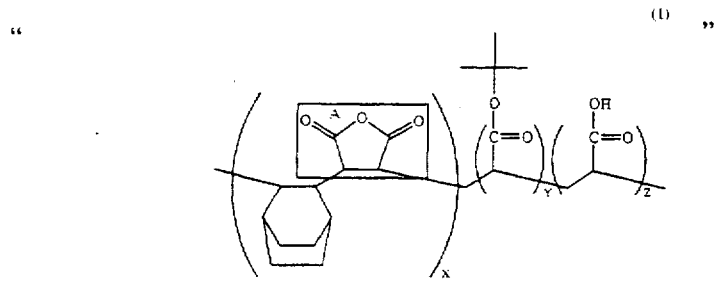

and insert --

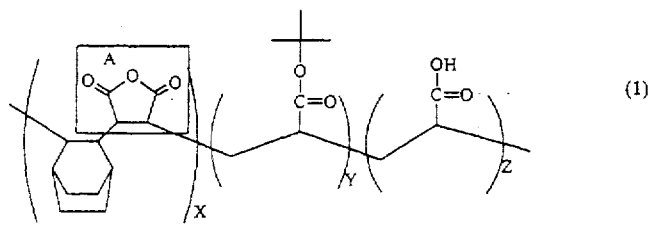

Column 9,
Line 9, after "40," delete "a" and insert -- % --.

Column 11,
Line 8, the phrase reading "catalyst, was removed by a filter" should read
- catalyst, was removed by a filter. --.

Column 21,
Line 24, the phrase reading "lymerized with an alicyclic olef in unit, has a physical" should read -- lymerized with an alicyclic olefin unit, has a physical --.

UNITED STATES PATENT AND TRADEMARK OFFICE
CERTIFICATE OF CORRECTION

PATENT NO. : 6,165,672
DATED : December 26, 2000
INVENTOR(S) : Jae Chang Jung; Keun Kyu Kong; Cheol Kyu Bok; Ki Ho Baik It is certified that error appears in the above-identified patent and that said Letters Patent is hereby corrected as shown below:

Column 22, claim 2,
Line 16, after "(3)" insert -- or (4) below --.
Lines 18-27, next to compound " 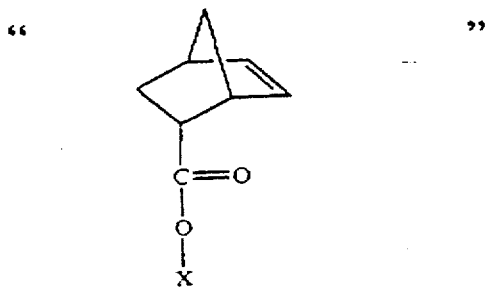 "

please insert -- (3) -- next to the drawing to identify the compound.

Column 22, claim 2,
Lines 18-27, next to compound (3), please insert the following compound and identify it by inserting -- (4) -- next to the drawing as shown.

-- 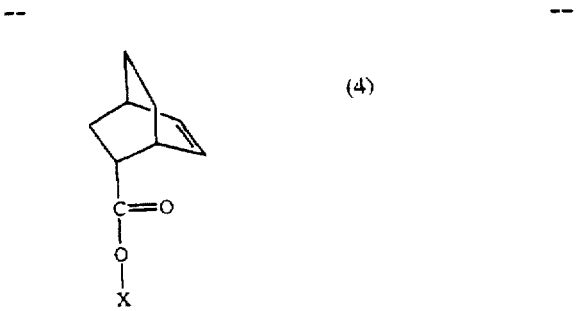 --

(4)

Column 22, claim 6,
Line 51, after the word "claim," delete "3" and insert -- 2 --.
Line 53, after "(3)," insert -- or (4) below --.

UNITED STATES PATENT AND TRADEMARK OFFICE
CERTIFICATE OF CORRECTION

PATENT NO. : 6,165,672
DATED : December 26, 2000
INVENTOR(S) : Jae Chang Jung; Keun Kyu Kong; Cheol Kyu Bok; Ki Ho Baik Page 3 of 4

It is certified that error appears in the above-identified patent and that said Letters Patent is hereby corrected as shown below:

Column 23, claim 6,
Lines 3-13, please delete the formula identified as (3):

" 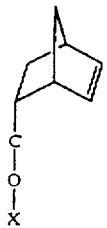 "

and insert -- 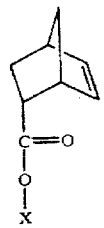 --

Column 23, claim 6,
Lines 3-13, next to the forumla identified as (3), insert the following formula and identify it by inserting -- (4) -- next to the drawing as shown.

-- 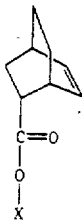 (4) --

Column 23, claim 11,
Line 41, after the word "alicyclic," delete "olef in-" and insert -- olefin --.

UNITED STATES PATENT AND TRADEMARK OFFICE
CERTIFICATE OF CORRECTION

PATENT NO.    : 6,165,672
DATED         : December 26, 2000
INVENTOR(S)   : Jae Chang Jung; Keun Kyu Kong; Cheol Kyu Bok; Ki Ho Baik It is certified that error appears in the above-identified patent and that said Letters Patent is hereby corrected as shown below:

Column 25, claim 16,
Line 12, delete "750° 1 C." and insert -- 75° C -.

Column 25, claim 17,
Line 17, delete "[3-maleimidepropyl 2" and insert -- [3-maleimidepropyl --.
Line 34, delete "60° 0C." and insert -- 60° C --.

Signed and Sealed this

Twelfth Day of February, 2002

Attest:

JAMES E. ROGAN
Attesting Officer      Director of the United States Patent and Trademark Office